United States Patent
Chen et al.

[11] Patent Number: 6,022,330
[45] Date of Patent: Feb. 8, 2000

[54] PREPARATION OF EASILY STRIPPED OFF TEMPORARY WOUND DRESSING MATERIALS BY RADIATION GRAFTING

[75] Inventors: Chia-Chieh Chen, Tao Yen Hsien; Ko-Shao Chen, Taipei; Te-Hsing Wu, Tao Yen City; Ching-Hohn Len, Taipei; Zei-Tsan Tsai, Chung Li; Bin Lin, Hua Lien, all of Taiwan

[73] Assignee: Institute of Nuclear Energy Research, Taiwan, R.O.C., Lung-Tan, Taiwan

[21] Appl. No.: 08/880,744

[22] Filed: Jun. 23, 1997

[51] Int. Cl.$^7$ ................ A61F 5/04; A61F 13/04
[52] U.S. Cl. ............... 602/8; 522/107; 522/120; 602/8
[58] Field of Search ............. 602/8, 41; 128/90; 522/107, 120

[56] References Cited

U.S. PATENT DOCUMENTS

| | | |
|---|---|---|
| 3,326,710 | 6/1967 | Brodie . |
| 3,421,501 | 1/1969 | Beightol ........................... 602/8 |
| 3,874,376 | 4/1975 | Dart et al. ....................... 128/90 |
| 4,277,242 | 7/1981 | McLaren . |

FOREIGN PATENT DOCUMENTS 1281457  11/1970  United Kingdom .

OTHER PUBLICATIONS

Henon, Yves Gamma Processing:The State of the Art Medical Device Technology pp. 30–37 Jun./Jul. 1992.

Primary Examiner—Richard J. Apley
Assistant Examiner—Kelvin Hart
Attorney, Agent, or Firm—Burns, Doane, Swecker & Mathis, LLP

[57] ABSTRACT

A novel method of preparation of easily stripped off temporary wound dressing material is disclosed. In this process, the-N-isopropyl acrylamide (NIPAAm) monomer is successfully grafted on the non-woven cloths by copolymerization. It is initiated by γ-ray irradiation to activate the surface of the non-woven cloth. NIPAAm is then grafted onto the surface of the non-woven cloth. The free radical or peroxide is produced by Co-60 γ-ray, then grafted on the non-woven cloths. The lower critical solution temperature (LCST) in thermoresponsive poly-N-isopropylacrylamide (NIPAAm) is still retained after the grafting. This will make the dressing cloth stripped off easily and without hurting the tissue. The material process is very simple and has medically applicable value.

11 Claims, 4 Drawing Sheets

PREPARATION OF EASILY STRIPPED OFF TEMPORARY WOUND DRESSING MATERIALS BY RADIATION GRAFTING

FIELD OF THE INVENTION

The present invention relates to method for preparing a dressing material and, more particularly, to a method for preparing easily stripped off wound dressing materials by radiation grating and the resulted dressing material can be readily stripped off from the tissue after the wound is cured. According to one aspect of the present invention, the poly-N-isopropylacrylamide (PNIPAAm)polymer is successfully grafted onto the surface of a non-woven cloth through copolymerization.

DESCRIPTION OF PRIOR ART

A major drawback in a conventional dressing material, mainly composed of gauze, is the adhering between the fibers of the gauze material and the tissue. When the fibers of the gauze are enclosed by the newly grown tissue as the wound is cured, the separation between the dressing material and the tissue becomes very difficult. If the separation is not correctly performed, a secondary damage to the wound will be experienced and the recovery is also prolonged.

Generally, the dressing material applied to and covering the wounded area resulted from burning or scratching must be capable of absorbing the exuded liquid from the wounded area. On the other hand, this dressing material also serves as an excellent barrier which provides an intact environment such that the wounded tissue can be prevented from being infected by external bacteria or virus while the wounded tissue may recover to its original condition.

The non-woven is featured with porosity, larger surface area with no dust, and being easily processable and the surface mechanism readily modifiable and it can readily be conditioned to serve as an excellent dressing material. However, the fibers of the non-woven can be readily enclosed by the tissue when it is cured. If the separation therebetween is not suitably performed, a secondary injury to the wound can be experienced.

The poly-N-isopropylacrylamide is a temperature-sensitive polymer and when dissolved in water it has a lower critical solution temperature (LCST) of about 32° to 33° C. Since human body has a higher temperature than this transition temperature and when this poly-N-isopropylacrylamide is applied onto the surface of skin, the polymer becomes hydrophobic as water emerges, thereby facilitating its being readily stripped off from the skin.

Graft-copolymerization through radiation grafting has been widely applied in the plastic industry. H. C. Hsieh et al propose in a paper entitled "Surface-grafting copolymerization of thermo-responsive N-isopropylacrylamide onto polymers" to use N-isopropyl acrylamide which can be grafted onto the surface of a modified film through UV light to improve the hydrophilic and slippery property and the resulted film can be applied on medical catheter.

H. T. Lokhande et al have also suggested using acrylic nitrile for grafting by γ-ray irradiation onto a plastic layer. However, no suggestion has ever been disclosed to graft the poly-N-isopropylacrylamide coating onto the surface of a non-woven dressing material through UV light or radiation grafting.

SUMMARY OF THE INVENTION

Accordingly, it is an object of the present invention to provide a dressing material coated with a layer of poly-N-isopropylacrylamide through radiation graft-copolymerization. When a separation between the dressing material and the tissue is required, the dressing material can be firstly immersed in a low-temperature water to expand as absorbing water and become hydrophobic such that the non-woven dressing can be readily stripped off from the tissue of the wound. The secondary injury and pain accompanied can be therefore reduced or even eliminated.

According to one aspect of the invention, the radiation, such as γ-ray, provides a sterilization effect and no initiator is required for the copolymerization. No environmental pollution and biological toxic substances are generated.

According to one aspect of the present invention, a novel dressing material is provided in which the substrate of non-woven cloth is immersed in the solution of N-isopropylacrylamide (PNIPAAm) monomer. Then a high energy γ-ray irradiation is introduced such that the N-isopropylacrylamide monomer is grafted onto the surface of the non-woven cloth during the exposure of the γ-ray to thus form a dressing material.

According to another aspect of the present invention, a novel dressing material is provided in which still a non-woven cloth is used as the substrate and immersed in the solution of NIPAAm monomer. The NIPAAm monomer is grafted on the surface of the non-woven cloths by the radiation of UV light to the dressing material.

According to another aspect of the present invention, a novel and simple method for making a dressing material is provided using non-woven cloths as substrate, in which the substrate is first treated with electric plasma and then immersed into the NIPAAm monomer solution into which an additive to prevent oxidation during the reaction is added, and nest by irradiation with γ-rays or UV light, a PNIPAAm polymer coating is formed on the surface of the non-woven cloth through graft-copolymerization and a dressing material is thereby formed. When radiation with γ-ray or UV light is exposed onto the non-woven cloths immersed in the solution of N-isopropylacrylamide monomer, a high energy is produced breaking bondings on the surface of non-woven cloths whereby free radical or peroxide is produced. However, as antioxidant is added, which prevents any oxidation from taking place between the free radical and air and the free radical is joined by bonding to the N-isopropylacrylamide monomer forming PNIPAAM with excellent compatibility, water absorption and temperature sensitivity to be grafted to the non-woven cloth, the low-temperature (<32° C.) hyrophile of the material, therefore, renders it to be easily stripped off, hence it being easily stripped off temporary wound dressing materials.

DETAILED DESCRIPTION OF PREFERRED EMBODIMENT

According to the present invention, a widely used non-woven fabric is used as the substrate and this substrate can be pre-treated or not with a plasma. The substrate is firstly immersed into a solution of N-isopropyl acrylamide monomer (NIPAAm) into which is added an additive which prevents oxidation from taking place between the free radical produced during the reaction and the air. Then the substrate is exposed to irradiation by γ-ray or UV light source such that NIPAAm is grafted by copolymerization onto the surface of the substrate.

Thus, an easily stripped-off dressing material having an excellent compatibility with human tissue, liquid absorbing capability, and hydrophilicity at low temperature.

The non-woven fabric used can be fiber non-woven cloths of PET, rayon, nylon, polyester, PP or PA.

The radiation dose of the γ-ray is preferably less then 100 kGy, however it must not be lower than 10 kGy. The time, of γ-irradiation is from 2 to 20 hours.

When the UV light is used as the radiation source, the duration is preferably from 10 to 90 minutes, and most preferably from 40 to 60 minutes.

The NIPAAm monomers can be also replaced by compounds with a close structure and property, such as: N,N'-diethyl-acrylamide monomer (DEAAm), acrylroyl pyrrolidine (Apy).

The concentration of the above described monomer solution is preferable to be lower than 15%.

As for the antioxidant additives, in addition to the vitamin B2 solution, similar compounds can be also used to replace the vitamin B2 solution, and the concentration is preferably from 5 to 60%.

Figure 1:
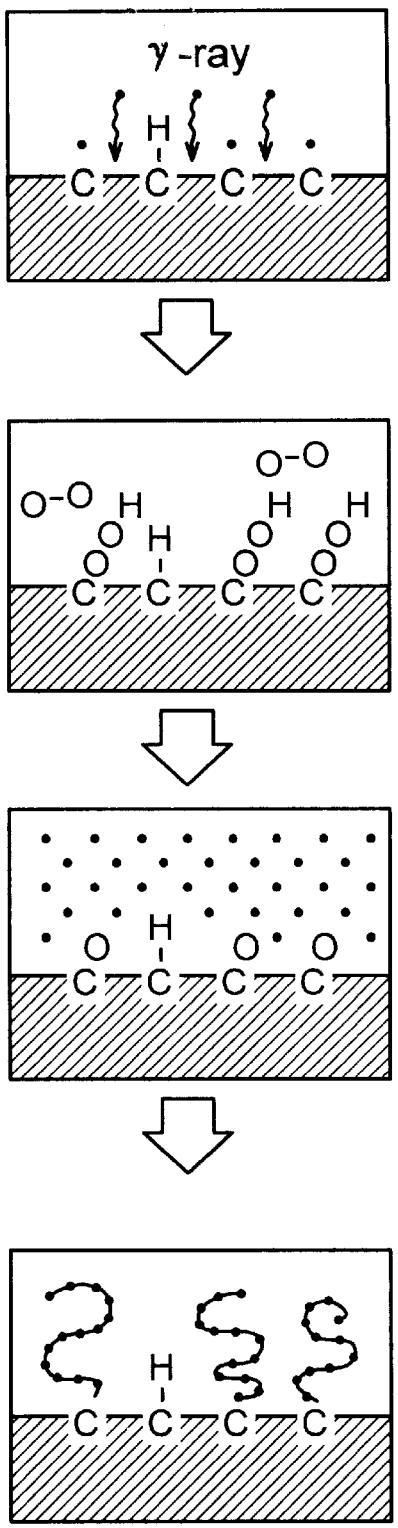
FIG. 1 is a schematic illustration showing the reaction mechanism of graft copolymerization of NIPAAm on surface by radiation with γ-ray in accordance with the present invention.
Figure 2A:
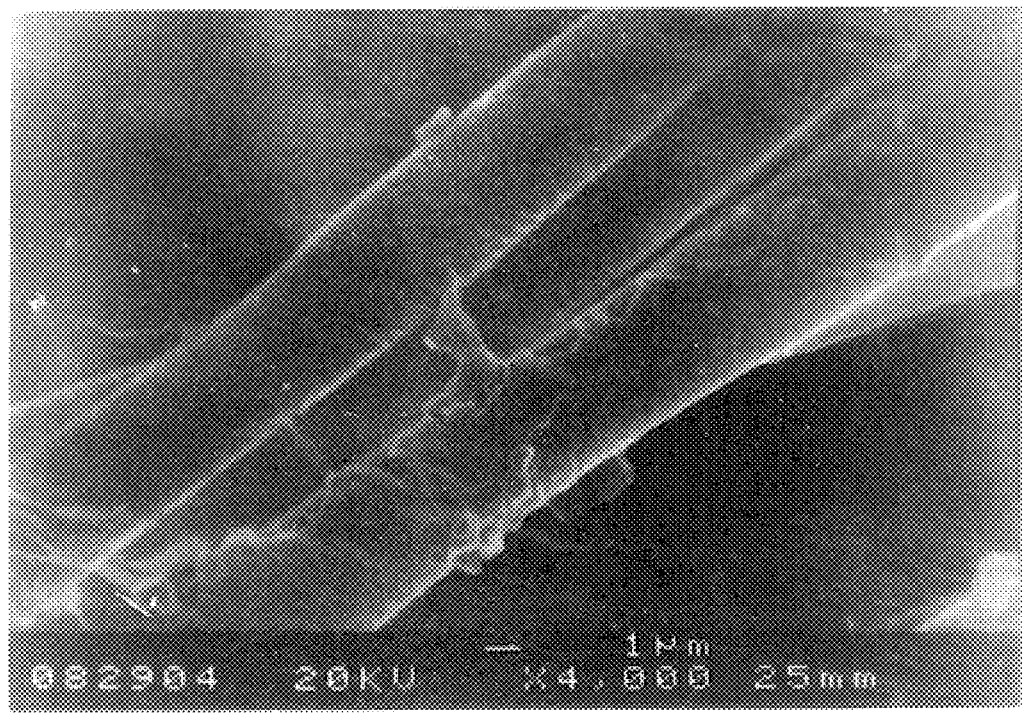
FIG. 2 are electronic microscopically scanning photos of the surface of the dressing materials prepared by the method of the present invention, in which 2(A) and 2(D) indicate that the substrate has been previously pre-treated with plasma and 2(C) shows the state of grafting by radiation with γ-ray the surface untreated with plasma.

EXAMPLE 1

γ-ray irradiation grafting of the plasma-treated non-woven fabric:

A test piece of PET non-woven substrate of a dimension of 1×4 cm and an average diameter of the fibrils of 3.5μ was pre-treated and activated with a plasma instrument, available from Samco Co., at the power of 10–50 W under an argon atmosphere of <0.2 torr for 2 to 10 minutes. By this process, peroxide or active species was produced on the surface of the substrate. Thereafter, the test piece was placed within a test tube upon completion of the surface treatment. About 20 cc of 10% NIPAAm and 50% vitamin B2 as oxidation inhibitor were poured into the tube. The tube was then sealed and exposed to γ-ray irradiation of less than 100 kGy for grafting. The time of γ-irradiation is from 2 to 20 hours. After grafting, the non-woven fabric test piece was washed with fresh water for 24 hour till the and the residue monomer were removed. Then the test piece was dried and then observed under the electron microscope scanner for the state of its surface. The result of observation on the surface is shown in FIG. 2(A).

Figure 2B:
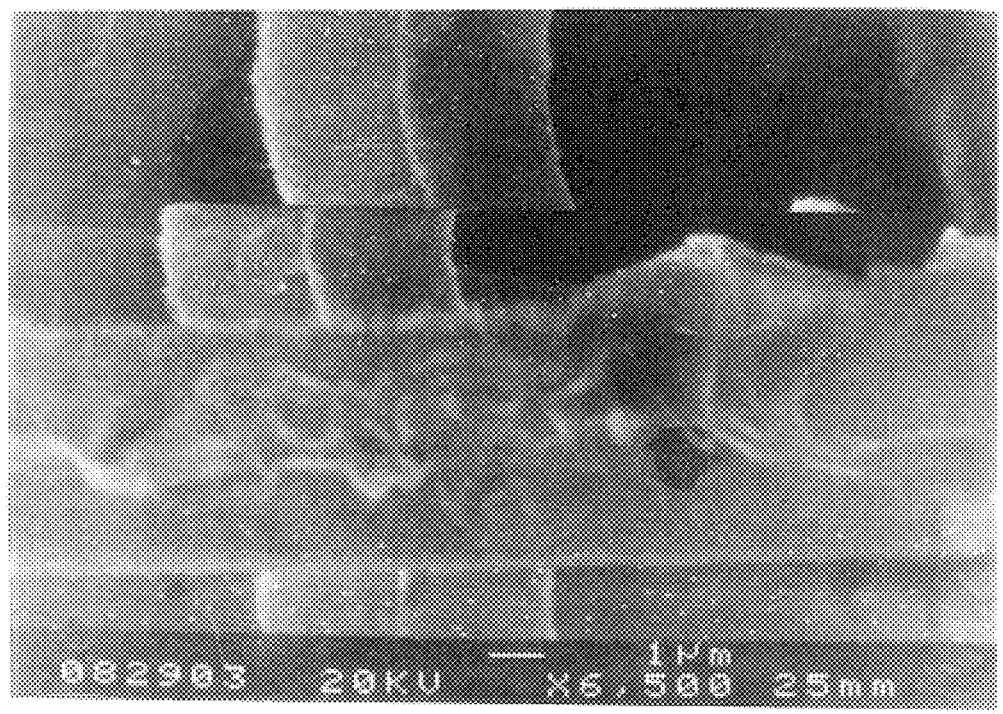

EXAMPLE 2

γ-ray irradiation grafting of the plasma-treated non-woven fabric:

A sample of non-woven substrate of 1×4 cm identical to Example 1 was taken and after treatment with a plasma instrument the sample substrate was directly immersed into a test tube containing about 20 cc of 5% NIPAAm and 25% vitamin B2 solution as oxidation inhibitor. The tube was then sealed and exposed to irradiation of a γ-ray irradiation of less than 100 kGy for grafting. The time of γ-irradiation is from 2 to 20 hours. After grafting the non-woven fabric test piece was then washed with fresh water for 24 hours till the homopolymers and the residue monomer are removed. After cleaning, the test piece thus obtained was dried and then observed under the electron microscope scanner for the state of its surface. The result of observation on the surface is shown in FIG. 2(B).

Figure 2C:
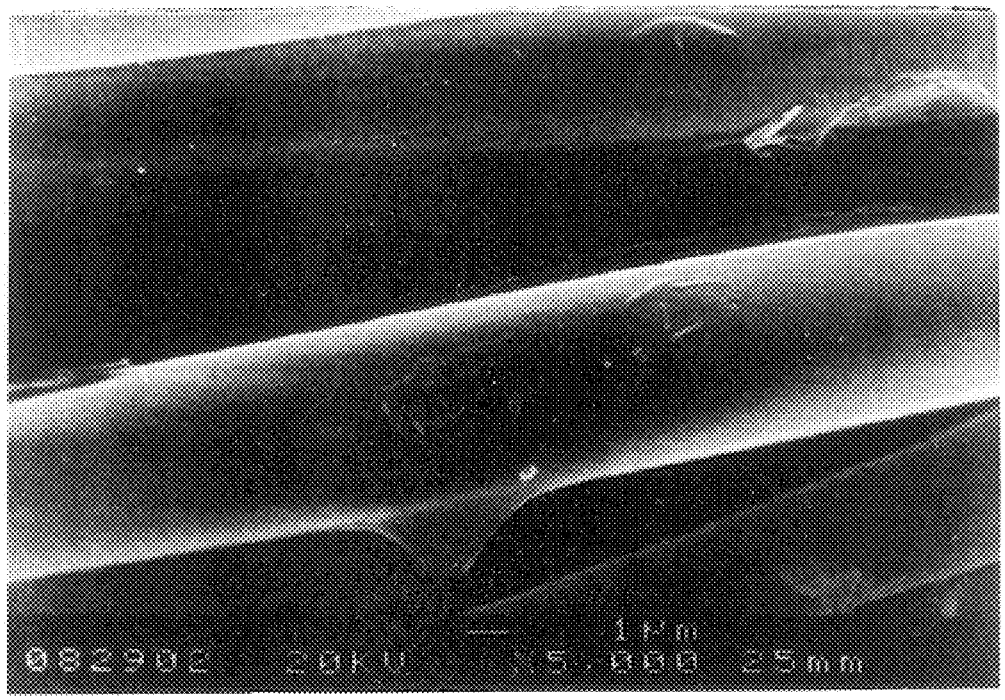

EXAMPLE 3

γ-ray irradiation grafting of a non-woven fabric untreated with plasma:

A test piece of non-woven substrate of a dimension of 1×4 cm was placed in a test tube, into which were poured about 20 cc of 5% NIPAAM and 25% vitamin B2 solution as oxidation inhibitor. The tube was then sealed and exposed to irradiation of a γ-ray radiation dose of less than 100 kGy for grafting. The time of γ-irradiation is from 2 to 20 hours. After grafting, non-woven fabric test piece was washed with fresh water for 24 hours till the homopolymers and the residue monomer were removed. After cleaning, the test piece thus obtained was dried and then observed under the electron microscope scanner for the surface. The result of observation on the surface is shown in FIG. 2(C).

EXAMPLE 4

Figure 3:
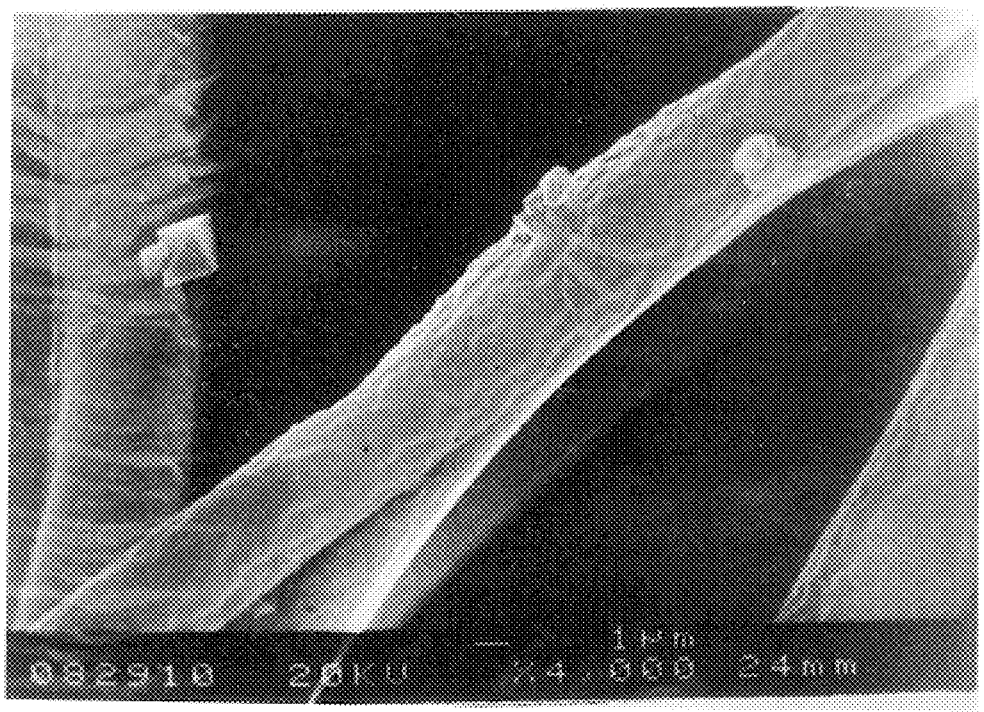
FIG. 3 is an electronic microscopically scanning photo of the surface of the dressing material prepared by the method of the present invention showing the state of grafting by radiation with UV light on the surface, where the substrate has been pre-treated with plasma.

In order to compare the results of graft-copolymerization performed on the non-woven fabric that were exposed to γ-ray irradiation and the non-woven fabric that were exposed to UV light irradiation, a test piece of 1×4 cm non-woven fabric substrate of same material was taken and was pre-treated and activated with a plasma at the power of 10–50 W under an argon atmosphere of <0.2 torr for 2 to 10 minutes. With this process, peroxide or active species was produced on the surface of the substrate. Thereafter, the sample was placed in a culture dish upon completion of the surface treatment, 45 cc of 5% NIPAAm and 25% vitamin B2 were poured into the dish to immerse the non-woven fabric in the solution. The dish was next placed on a rotating platform and exposed to radiation with an UV light of Osram 30 OW for about 20 minutes for grafting. When grafting was completed, the test piece of non-woven cloth was then washed with fresh water for more than 24 hours till the homopolymers and the residue monomer were removed. The test piece was then dried after cleaning and was observed under the electron microscope scanner for its surface. The result of observation on the surface is shown in FIG. 3.

COMPARISON EXAMPLE

In order to compare the state of grafting on the surface of the non-woven fabric treated by the method of the present invention and the non-woven fabric that has not been subjected to any treatment, a test piece of untreated non-woven cloth of the same material was next taken and treated according to the same process of treatment described in Example 3. However, no test piece was exposed to the radiation of γ-ray irradiation. The test piece thus obtained after cleaning and drying was then observed under the above described scanner for its surface. The result of observation is shown in FIG. 4.

Figure 4:
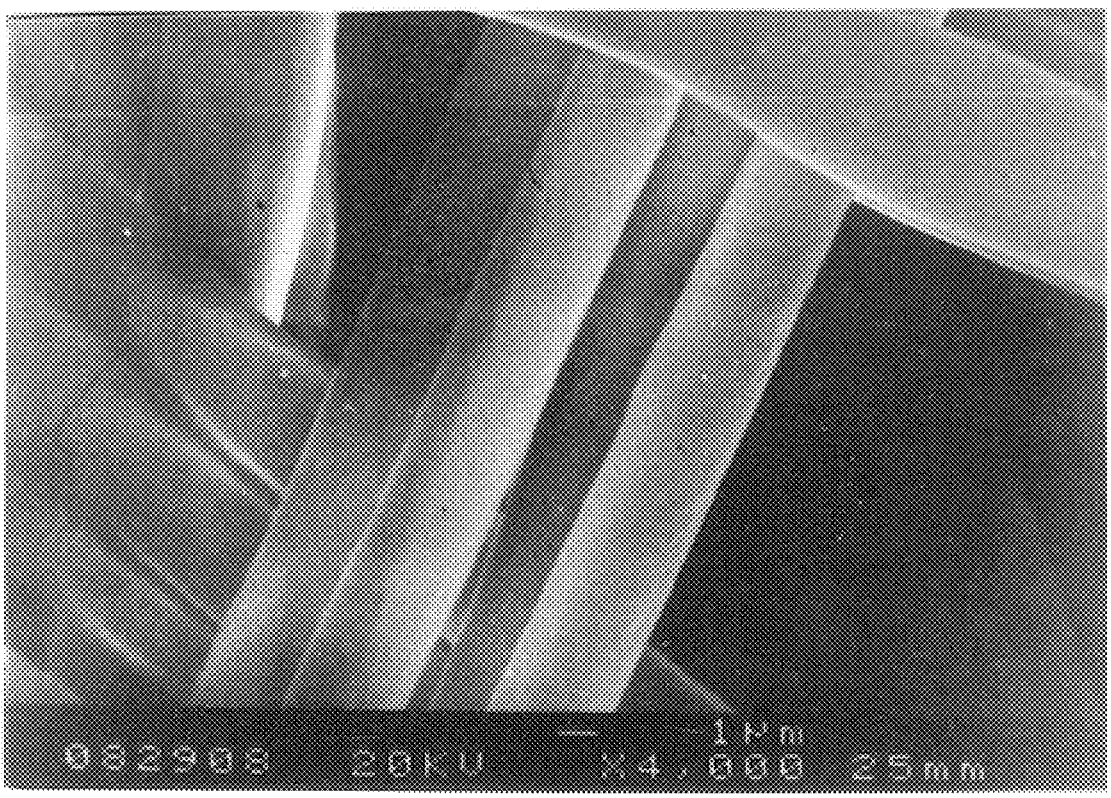
FIG. 4 is an electronic microscopically scanning photo showing the state of grafting on the untreated surface of a non-woven cloth.

As shown in FIGS. 2(A), 2(B), 2(C) and FIG. 3, surfaces of non-woven cloths that have been treated according to the method of the present invention all show well graft polymerization, whereas, the test piece of FIG. 4 has a smooth surface, which shows that no action of graft polymerization has taken place.

From the foregoing description of examples, it shows that radiation whether by γ-ray irradiation or UV light all can accomplish the grafting successfully. On the other hand, the plasma treatment process may also effect the wicking time of the non-woven fabric test piece. The result is shown in Table 1.

From the hydrophilicity of non-woven cloth results of Table 1, it can be readily found that the, graft-copolymerization is easily carried out as it was subjected to plasma treatment and exposed to radiation of UV light.

Again, a test piece of non-woven fabric was pretreated with plasma and then grafting was performed by exposing the test piece to radiation with an UV light source. Otherwise, test piece of non-woven fabric that had been treated with plasma or test piece of non-woven fabric that had not been treated with plasma were exposed to radiation with a γ-ray irradiation and grafting was performed. The hydrophilicity is shown in Table 2 and Table 3.

From Table 2, the best conditions for UV light grafting reaction are pretreatment with plasma for 5 minutes and then exposure to UV light source for 60 minutes.

Table 3 shows that the results of grafting through γ-ray were independent of whether the non-woven cloths had been pretreated with plasma or not with plasma.

From Tables 1, 2 and 3, it shows that although the test pieces after subjecting to grafting through γ-ray irradiation have a longer wicking tine than the test pieces that are subjected to grafting by radiation of UV light, the test pieces after subjecting to grafting have a better result and are more cleaned than those subjecting to grafting by radiation of UV light. There is also a saving of washing time for the test piece. Thus, grafting by γ-ray irradiation process is the most simple and effective.

Advantages associated with the present invention include:

1. According to the present invention, materials used are mainly the inexpensive non-woven fabrics as the substrate plus a small amount of NIPAAm and vitamin B2, the manufacturing cost is therefore low while the economic value is high.

2. The method of the present invention uses radiation by γ-ray irradiation or UV light in the graft-polymerization of NIPAAm to form dressing materials. The preparation process is simple and the products are of an excellent quality.

3. The dressing material made according to the present invention has a better result over the conventional gauze. The dressing material can be readily stripped off from the tissue when applied to ordinary cut or wound. No secondary injury will be experienced and the wound tissue heal quickly.

TABLE 1

Influence of the wicking time for pretreatment with plasma on grafting with UV light

| Time for Plasma treatment | 0 min | 2 mins | 5 mins | 7 mins | 10 mins |
|---|---|---|---|---|---|
| Wicking time at 23.5° C. in seconds | 7200 | 60 | 34 | 35 | 40 |
| Wicking time at 37.0° C. in seconds | 5400 | 162 | 118 | 74 | 103 |

Note: Treatment by radiation with UV light for 90 minutes.

TABLE 2

Influence of the time for UV light grafting on wicking property of the test piece product

| Time for UV light grafting | 30 mins | 45 mins | 60 mins | 90 mins |
|---|---|---|---|---|
| Wicking time at 23.5° C. in seconds | 30 | 21 | 15 | 34 |

Note: Pre-treatment with plasma for 5 minutes.

TABLE 3

Effect of plasma pretreatment through γ-ray irradiation grafting of NIPAAm on test piece of the non-woven fabric

| Method | Wicking time (seconds) |
|---|---|
| Untreated with plasma | 40–50 |
| Treated with plasma | 40–50 |

We claim:

1. A method for producing a wound dressing material which can be easily removed from a wound surface after application thereto comprising the following steps:
   (i) immersing a non-woven fabric substrate with a solution containing at least one monomer selected from the group consisting of N-isopropylacrylamide monomer (PNIPAAm), N,N'-diethylacrylamide (DEAAm), and acryloyl pyrrolidine (APY);
   (ii) exposing said substrate and said monomer-containing solution to γ-ray radiation ranging from 10 to 100 kGy or UV irradiation after plasma pretreatment of said non-woven fabric substrate such that said monomer becomes grafted by copolymerization onto the surface the fibers which comprise said non-woven fabric substrate; and
   (iii) subsequently washing and drying the resultant non-woven fabric substrate to which is grafted said monomer via copolymerization to produce a wound dressing material which can be applied to a wound and easily removed therefrom after application.

2. The method of claim 1, wherein said monomer is an N-isopropylacrylamide monomer.

3. The method according to claim 1, wherein the concentration of the monomer contained in said monomer-containing solution is lower than 15 weight percent.

4. The method according to claim 1, wherein said monomer solution further comprises an additive which inhibits oxidation between free radical and oxygen which are contained in said monomer solution.

5. The method according to claim 4, wherein said additive is vitamin B2.

6. The method according to claim 1, wherein said monomer is an acryloyl pyrrolidone (APY) monomer.

7. The method according to claim 1, wherein said monomer is an N,N'-diethylacrylamide (DEAAm) monomer.

8. The method according to claim 1, wherein said irradiation comprises UV light irradiation and said non-woven fabric substrate is pretreated by activation with a plasma instrument prior to UV light irradiation.

9. The method according to claim 8, wherein the time of exposure to UV light irradiation ranges from 10 to 90 minutes.

10. The method according to claim 8, wherein said substrate is pretreated with plasma at a power ranging from 10 to 50 W under an argon atmosphere which is less than 0.2 Torr for about 2 to 10 minutes.

11. The method of claim 1, wherein said non-woven fabric substrate is a polyester material.

* * * * *